United States Patent [19]

Jardillier et al.

[11] 4,329,346

[45] May 11, 1982

[54] PHARMACEUTICAL COMPOSITIONS CONTAINING 2,6-BIS-(DIETHANOLAMINO)-4-PIPERIDINO-PYRIMIDO[5,4-d]PYRIMIDINE

[75] Inventors: Jean-Claude Jardillier, Reims; Yves Carpentier, Rilly la Montagne; Bernard Desoize, Reims, all of France

[73] Assignee: Boehringer Ingelheim GmbH, Ingelheim, Fed. Rep. of Germany

[21] Appl. No.: 170,913

[22] Filed: Jul. 21, 1980

[30] Foreign Application Priority Data

Aug. 3, 1979 [DE] Fed. Rep. of Germany ....... 2931573

[51] Int. Cl.$^3$ ............................................ A61K 31/505
[52] U.S. Cl. .................................................... 424/251
[58] Field of Search ........................................ 424/251

[56] References Cited

PUBLICATIONS

Chemical Abstracts, 89:70986n (1978).

*Primary Examiner*—Jerome D. Goldberg
*Attorney, Agent, or Firm*—Hammond & Littell, Weissenberger & Muserlian

[57] ABSTRACT

This invention is directed to a pharmaceutical composition for inhibiting the growth of L-1210 leukemia cells which comprises as active ingredient 2,6-bis-(diethanolamino)-4-piperidino-pyrimido[5,4-d]pyrimidine or a pharmacologically acceptable acid addition salt thereof, and one or more pharmaceutical carriers or diluents.

2 Claims, No Drawings

PHARMACEUTICAL COMPOSITIONS CONTAINING 2,6-BIS-(DIETHANOLAMINO)-4-PIPERIDINO-PYRIMIDO[5,4-d]PYRIMIDINE

This invention is directed to pharmaceutical preparations containing 2,6-bis-(diethanolamino)-4-piperidino-pyrimido[5,4-d]pyrimidine. More particularly, this invention is directed to pharmaceutical preparations containing 2,6-bis-(diethanolamino)-4-piperidino-pyrimido[5,4-d]pyrimidine, or a pharmacologically acceptable acid addition salt thereof, and the use of such preparations in inhibiting the growth of L-1210 leukemia cells in animals.

It is known from the literature that the compound 2,6-bis-(diethanolamino)-4-piperidino-pyrimido[5,4-d]pyrimidine and its pharmacologically acceptable acid addition salts inhibit the attachment of tumor cells to the endothelium of vessels due to their inhibiting effect on thrombocyte aggregation and thus prevent the formation of metastasis. [See, for example, H. Gastphar et al. in Acta Med. Scand., 190, 269–271, 525 (1971) and Med. Welt, 23, 606–608 (1972), incorporated herein by reference.]. It has now surprisingly been found that 2,6-bis-(diethanolamino)-4-piperidino-pyrimido[5,4-d]pyrimidine and its pharmacologically acceptable acid addition salts inhibit the growth of cancer cells, for example, leukemia cells.

The inhibiting effect on the growth of leukemia cells, for example, has been demonstrated in the following manner:

1. Influence of 2,6-bis-(diethanolamino)-4-piperidino-pyrimido[5,4-d]pyrimidine on the multiplication of L 1210 tumor cells in cell cultures:

Under suitable cell culture conditions L 1210 cells (Y. Carpentier et al., 1978) show an exponential growth rate and double their number 2.23 ($\pm 0.21$) times every 24 hours (average value$\pm$SEM from 16 experiments in triplicate). When 2,6-bis-(diethanolamino)-4-piperidino-pyrimido-[5,4-d]pyrimidine was administered in a final concentration of $1 \times 10^{-4}$ mole/liter to the nutrient liquid of the cell culture, a reduced growth rate was obtained. This growth rate then amounted to 1.98 ($\pm 0.25$) cell multiplications every 24 hours (average value$\pm$SEM from 6 experiments in triplicate.) (The 50% inhibiting dose was $2 \times 10^{-4}$ mole/liter.) The difference in growth rates is highly significant from a statistical point of view ($p = 0.0002$).

2. Cytotoxic effect on L 1210 cells in vitro:

The compound 2,6-bis-(diethanolamino)-4-piperidino-pyrimido[5,4-d]pyrimidine in a final concentration of $1 \times 10^{-3}$ mole/liter killed L 1210 tumor cells in a cell culture. In so doing, 5% of the cells were killed within 4 hours. This percentage rose quickly to a value of 50% after 8 hours and reached a quota of 90% of cells killed after an incubation time of 12 hours. The $LD_{50}$ for the 24-hour cell culture was $5 \times 10^{-4}$ M.

The compound 2,6-bis-(diethanolaminio)-4-piperidino-pyrimido[5,4-]pyrimidine can be prepared in known manner. Suitable pharmacologically acceptable acid addition salts can be prepared by reaction with inorganic or organic acids.

According to this invention, pharmaceutical preparations containing 2,6-bis-(diethanolamino)-4-piperidino-pyrimido[5,4-d]pyrimidine are useful in retarding or inhibiting the growth of cancer cells. Eradication of cancer cells can be achieved in some instances. Such pharmaceutical preparations are, more specifically, useful in inhibiting the growth of L-1210 leukemia cells in animals.

Relatively large amounts of 2,6-bis-(diethanolamino)-4-piperidino-pyrimido[5,4d]pyrimidine must be administered to achieve the desired inhibiting effect upon the growth of L-1210 leukemia cells. However, due to the good compatibility, that is, the low toxicity and pharmacological acceptability, of 2,6-bis-(diethanolamino)-4-piperidino-pyrimido[5,4-d]pyrimidine, administration of large amounts is feasible. By way of example, it can be noted that the peroral acute toxicity of 2,6-bis-(diethanolamino)-4-piperidino-pyrimido[5,4-d]pyrimidine is 465 mg/kg in mice, $>3$ g/kg in rats, and $>3$ g/kg in guinea pigs.

The compound 2,6-bis-(diethanolamino)-4-piperidino-pyrimido[5,4-d]pyrimidine and pharmacologically acceptable acid addition salts thereof can be incorporated into conventional pharmaceutical preparations, such as tablets, coated tablets, capsules, suppositories, capsules, suspensions, solutions, powders, or ampules. For this purpose 2,6-bis-(diethanolamino)-4piperidino-pyrimido[5,4-d]pyrimidine and pharmacologically acceptable acid addition salts with inorganic or organic acids can be processed with other active ingredients and/or conventional pharmaceutical carriers or diluents. The daily dose required for pharmaceutical application is from about 50 to 100 mg/kg, that is, depending on the weight of the human patients to be treated, from about 1.6 to 8 g, preferably from about 2 to 6 g, distributed over 3 to 4 doses. The single dose is therefore from about 0.4 to 2 g, preferably from about 0.5 to 1.5 g, 3 to 4 times daily.

The following examples are intended to illustrate the invention and are not to be construed as limiting the invention thereto.

EXAMPLES

EXAMPLE 1

Capsules with 400 mg of 2,6-bis-(diethanolamino)-4-piperidino-pyrimido[5,4-d]pyrimidine Composition of one capsule:

| Component | Amount (mg) |
| --- | --- |
| Active substance | 400.0 |
| Corn starch | 80.0 |
| Lactose | 18.0 |
| Magnesium stearate | 2.0 |
| | 500.0 |

Preparation

The ingredients are mixed homogeneously and filled on a capsule filling machine into hard gelatine capsules of size 00, the capsule filling weight being checked continuously. If necessary, the capsules are then polished.

Capsule filling: 500 mg
Capsule size: 00

EXAMPLE 2

Coated tablets with 500 mg of 2,6-bis-(diethanolamino)-4-piperidino-pyrimido[5,4-d]pyrimidine Composition of one coated tablet core:

| Component | Amount (mg) |
|---|---|
| Active substance | 500.0 |
| Lactose | 50.0 |
| Corn starch | 40.0 |
| Polyvinyl pyrrolidone | 8.0 |
| Magnesium stearate | 2.0 |
| | 600.0 |

Preparation

The active substance, lactose, and starch are mixed and moistened homogeneously with the binding agent dissolved in water. The granulated mass is dried, screened, and mixed with the lubricant. The finished mixture is pressed to coated tablet cores.

Die: 12 mm, round biconvex

Coating

The above-described cores are coated in a coating vessel with a sugar paste up to 660 mg and subsequently with sugar syrup up to 680 mg.

EXAMPLE 3

Granulate with 4 g of 2,6-bis-(diethanolamino)-4-piperidino-pyrimido[5,4-d]pyrimidine per portion

| Component | Amount (mg) |
|---|---|
| Active substance | 4,000.0 |
| Corn starch | 500.0 |
| Cane sugar | 500.0 |
| | 5,000.0 |

Preparation

The active substance and corn starch are mixed homogeneously and granulated with a 70% solution of the sugar in water, and then the granulate is dried. After the powder ingredients have been screened, the granulate is covered with sugar syrup in a coating vessel.

EXAMPLE 4

Ampules with 500 mg of 2,6-bis-(diethanolamino)-4-piperidino-pyrimido[5,4-d]pyrimidine per 10 ml

| Composition of one ampule: | |
|---|---|
| Component | Amount |
| Active substance | 500.0 mg |

-continued

| Composition of one ampule: | | |
|---|---|---|
| Component | | Amount |
| Tartaric acid | | 130.0 mg |
| Sodium chloride | | 45.0 mg |
| Water (distilled) for injection purposes | q.s. ad | 10.0 ml |

Preparation

The active substance base and the iostonic agent, i.e., the sodium chloride, are dissolved in a previously prepared aqueous solution of the tartaric acid and sufficient distilled water to make up the final volume is added.

EXAMPLE 5

Infusion Solution with 8 g of 2,6-bis-(diethanolamino)-4-piperidino-pyrimido[5,4-d]pyrimidine per 500 ml

| Component | | Amount |
|---|---|---|
| Active substance | | 8,000.0 mg |
| 1 N HCl | | q.s. |
| 1 N NaOH sufficient for pH 5.5 | | q.s. |
| Sodium chloride | | 4,000.0 mg |
| Water (distilled) for injection purposes | q.s. ad | 500 ml |

Preparation

Hydrochloric acid is added to an active substance suspension with slight heating until complete dissolution of the active substance base. By addition of the main quantity of the distilled water for injection purposes, the solution is brought to room temperature, and the solution is adjusted to a pH of 5.5 with sodium hydroxide. After the sodium chloride has been dissolved, the solution is filled up to the final volume with water.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method for inhibiting the growth of L-1210 leukemia cells which comprises administering to an animal in need of such treatment an L-1210 leukemia cell growth inhibiting amount of a pharmaceutical composition comprising as active ingredient 2,6-bis-(diethanolamino)-4-piperidino-pyrimido-[5,4-d]pyrimidine or a pharmacologically acceptable acid addition salt thereof, and one or more pharmaceutical carriers or diluents.

2. The method of claim 1, wherein the pharmaceutical composition comprises as active ingredient 2,6-bis-(diethanolamino)-4-piperidino-pyrimido-[5,4-d]pyrimidine or a pharmacologically acceptable acid addition salt thereof, and pharmaceutical carrier or diluent.

* * * * *